(12) United States Patent
Kudrna

(10) Patent No.: US 9,874,510 B2
(45) Date of Patent: Jan. 23, 2018

(54) MAGNETIC CHIP DETECTOR/COLLECTOR

(71) Applicant: PRATT & WHITNEY CANADA CORP., Longueuil (CA)

(72) Inventor: Richard Kudrna, Carignan (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 666 days.

(21) Appl. No.: 14/134,837

(22) Filed: Dec. 19, 2013

(65) Prior Publication Data

US 2015/0177116 A1   Jun. 25, 2015

(51) Int. Cl.
| | |
|---|---|
| *G01N 15/10* | (2006.01) |
| *H01F 7/02* | (2006.01) |
| *G01N 33/28* | (2006.01) |
| *G01N 15/00* | (2006.01) |
| *H01F 7/00* | (2006.01) |

(52) U.S. Cl.
CPC ..... *G01N 15/1031* (2013.01); *G01N 33/2858* (2013.01); *H01F 7/0294* (2013.01); *G01N 2015/0053* (2013.01); *H01F 7/00* (2013.01)

(58) Field of Classification Search
CPC ............ G01N 15/1031; G01N 33/2858; H01F 7/0205; H01F 7/0252; H01F 7/0263; H01F 7/0294
USPC ................... 73/53.05, 61.42, 61.71
See application file for complete search history.

(56) References Cited

U.S. PATENT DOCUMENTS

| | | | | |
|---|---|---|---|---|
| 3,335,412 A | * | 8/1967 | Matsumoto | G11B 5/127 360/122 |
| 5,356,534 A | * | 10/1994 | Zimmerman | C02F 1/482 123/538 |
| 5,384,535 A | | 1/1995 | Mayeur | |
| 2004/0195931 A1 | * | 10/2004 | Sakoda | H02K 16/00 310/268 |
| 2007/0262028 A1 | | 11/2007 | Flaherty | |

FOREIGN PATENT DOCUMENTS

| | | | | |
|---|---|---|---|---|
| CN | 102436900 A | * | 5/2012 | ............ H01F 13/00 |
| WO | WO 2013/077729 | | 5/2013 | |

* cited by examiner

*Primary Examiner* — Peter Macchiarolo
*Assistant Examiner* — Anthony W Megna Fuentes
(74) *Attorney, Agent, or Firm* — Norton Rose Fulbright Canada LLP

(57) ABSTRACT

A magnetic chip device such as a chip detector or chip collector, comprising a horseshoe magnet held within a housing and having two adjacent tips protruding from the housing, and having a plurality of portions extending sequentially from one of the tips to the other, the plurality of portions including two end portions, each one of the two end portions extending to a corresponding one of the tips, and a rare-earth magnet portion made of a rare earth magnet material and positioned between the two end portions in the sequence.

20 Claims, 5 Drawing Sheets

MAGNETIC CHIP DETECTOR/COLLECTOR

TECHNICAL FIELD

The application relates generally to chip devices such as chip collectors or detectors typically used to obtain indications of a presence of metallic chips in the oil of gas turbine engines.

BACKGROUND OF THE ART

The use of chip devices is well established in the field of gas turbine engines where chip devices are used to obtain an indication of a presence of metallic chips in the oil of the gas turbine engine, which, in turn, can be associated to wear of engine components. More specifically, the warning obtained from chip devices can be used in triggering a preventive maintenance of the engine.

Although known chip devices were satisfactory to a certain degree, they also suffered from some limitations. More specifically, the magnet is magnetized during one of the final steps of the fabrication process, after integration into the housing. The additional magnetization step is undesirable from a manufacturing standpoint as it adds costs, and the magnet of known chip devices was subject to demagnetization upon exposure to extraneous magnetic fields, shock, vibration or the like. There thus remained room for improvement in addressing the aforementioned limitations.

SUMMARY

In one aspect, there is provided a gas turbine engine comprising an oil system and a magnetic chip device, the magnetic chip device comprising a magnet held within a housing and having two adjacent tips exposed to oil of the oil system, the magnet being generally U-shaped and having a plurality of portions extending sequentially from one of the tips to the other, following the U-shape, the plurality of portions including two end portions, each one of the two end portions extending to a corresponding one of the tips, and a rare-earth magnet portion made of a rare earth magnet material and positioned between the two end portions in the sequence.

In a second aspect, there is provided a magnetic chip device comprising a magnet held within a housing and having two adjacent tips protruding from the housing, the magnet being generally U-shaped and having a plurality of portions extending sequentially from one of the tips to the other, following the U-shape, the plurality of portions including two end portions, each one of the two end portions extending to a corresponding one of the tips, and a rare-earth magnet portion made of a rare earth magnet material and positioned between the two end portions in the sequence.

Further details of these and other aspects of the present invention will be apparent from the detailed description and figures included below.

DESCRIPTION OF THE DRAWINGS

Reference is now made to the accompanying figures, in which.

DETAILED DESCRIPTION

Figure 1:
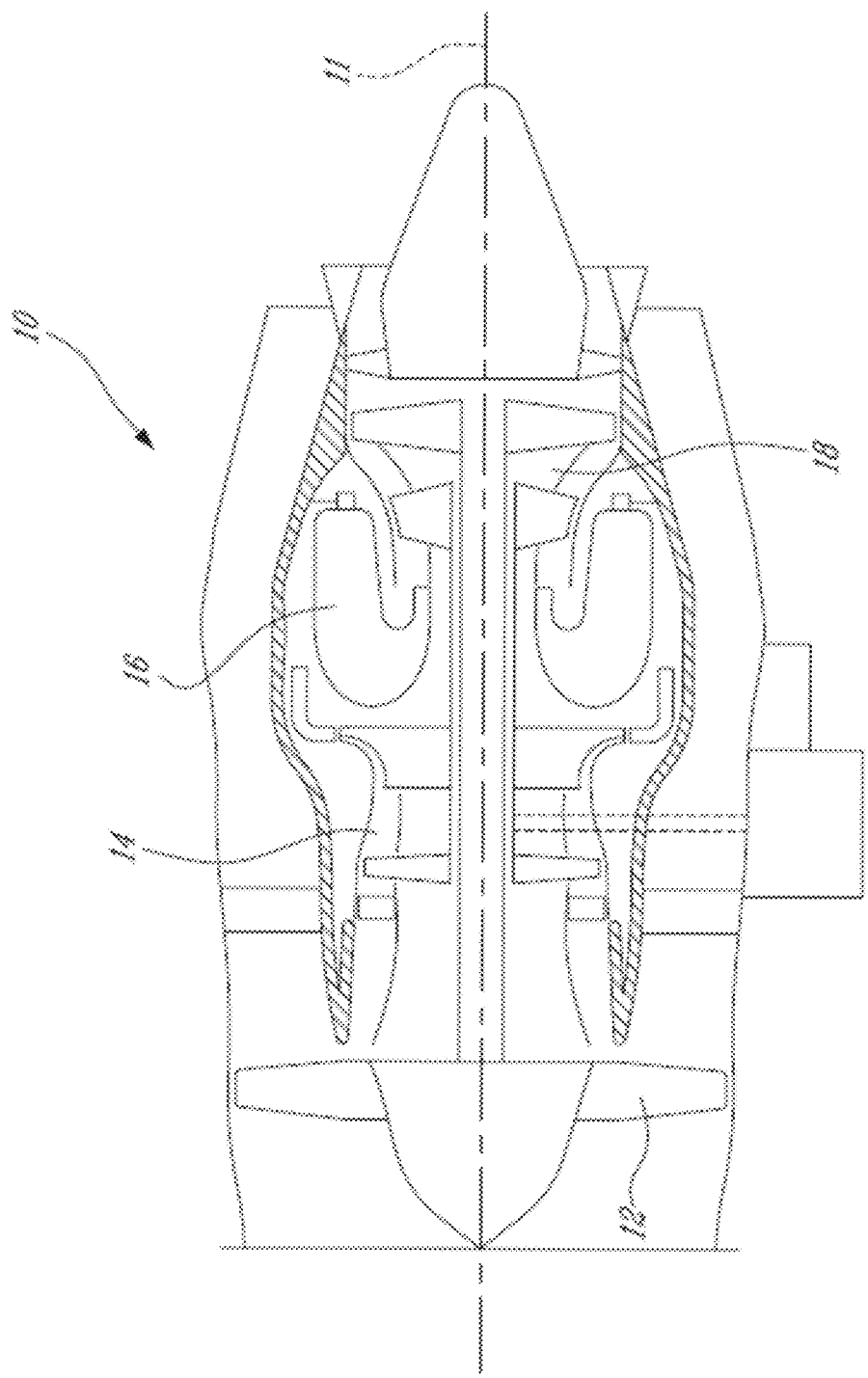
FIG. 1 is a schematic cross-sectional view of a gas turbine engine.

FIG. 1 illustrates a turbofan gas turbine engine 10 of a type preferably provided for use in subsonic flight, generally comprising in serial flow communication a fan 12 through which ambient air is propelled, a multistage compressor 14 for pressurizing the air, a combustor 16 in which the compressed air is mixed with fuel and ignited for generating an annular stream of hot combustion gases, and a turbine section 18 for extracting energy from the combustion gases. A buffer oil system having oil conduits or lines and oil compartments (not shown) is used to lubricate the bearings of the rotary components.

A chip device can be exposed to the oil to magnetically attract metal chips within the oil and allow their detection or isolation.

Several forms of chip devices are known. Perhaps the simplest is the chip collector, having one or two magnetic poles to catch metallic chips. The chip collector is often provided in the form of a plug which is snugly engaged in a wall of an oil compartment or oil conduit with the pole or poles exposed to the oil within, to collect metallic chips circulating in the vicinity of the collector. Maintenance technicians can remove the plug and visually inspect the magnetic pole or poles for chips when desired or deemed necessary, and therefore, a chip collector can be considered to be a manual form of chip detector.

Figure 2:
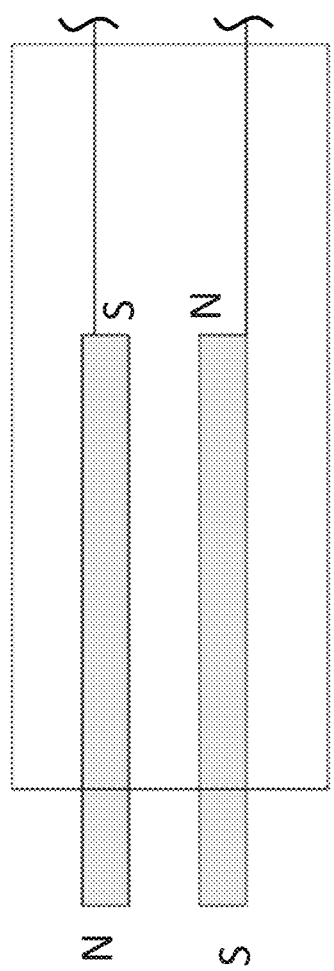
FIG. 2 is a schematic cross-sectional view of a chip detector in accordance with the prior art.

Typically nowadays, chip devices are provided in the form of automated chip detectors such as shown in FIG. 2 where two adjacent magnets (often referred to as a rod magnet pair) with adjacent, and magnetically inverted poles protruding from a housing are used in a configuration where the occurrence of a chip can bridge the gap between the two poles and close an electrical circuit therebetween. The two poles are electrically isolated from one another and independent wires can be used to check the continuity.

More elaborated chip detectors can use an additional pair of wires which can be used to test the chip device (i.e. to confirm that the absence of continuity is not caused by a malfunction of the chip device rather than by an absence of metallic chips), or in a 'Fuzz Burner' configuration where the additional pair of wires can be used to impart a current to burn light particles ('Fuzz') from the magnetic poles, for instance. Fuzz Burner operation can lead to spark erosion at the poles. As it will be understood from the discussion below, the teachings presented herein can be used in providing a chip device which has a relatively high resistance to spark erosion.

It was known to manufacture chip detectors such as shown in FIG. 2 by brazing lead wires onto anisotropic cast rod magnets in a fully demagnetized state, assembling with the housing, and magnetizing the rod magnet pair in a subsequent step. At least one significant reason for magnetizing in a subsequent step is to avoid having to fight with the magnet's mutual attraction. The arrangement leaves a large magnetic circuit gap at the rod ends internal to the unit, and the choice of ALNICO alloy results in an assembly which can be de-magnetized relatively easily, e.g. by wiping a sharp and magnetically permeable knife-like blade along the magnets, perhaps due to the imparted mechanical rumble and high accelerations at high frequency, while simultaneously shunting field through the blade. The additional step of magnetizing the rod magnet pair may be associated with additional costs.

Figure 3:
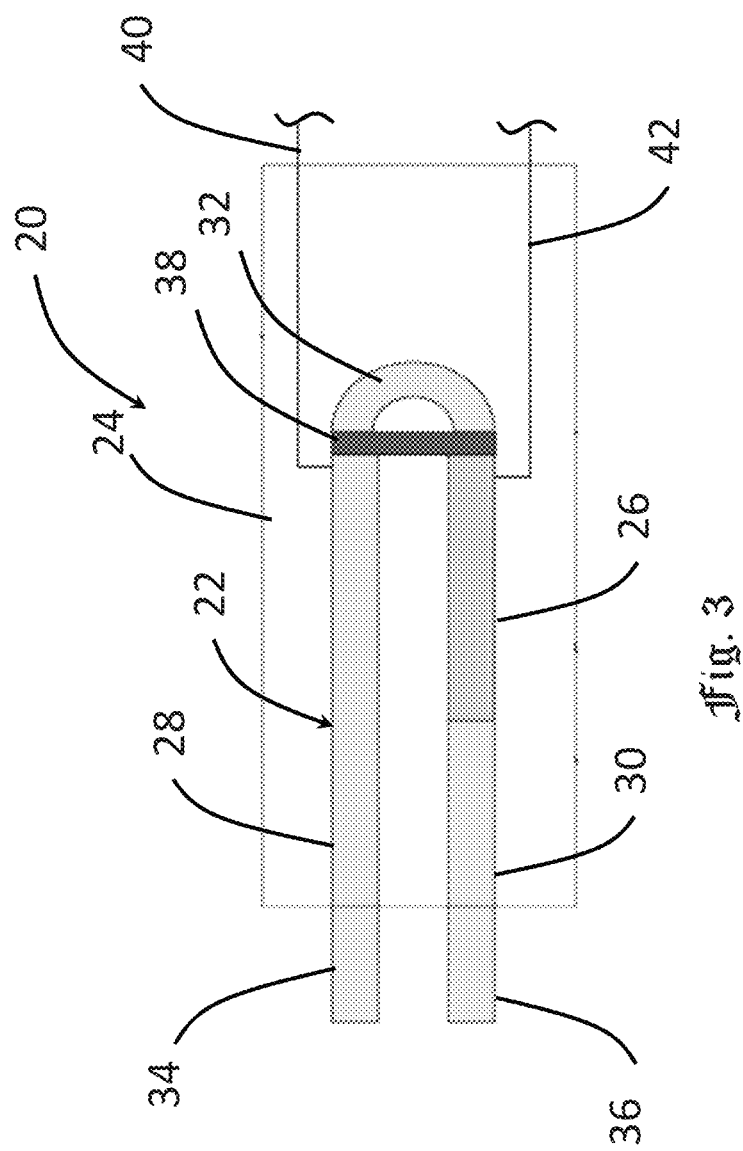
FIG. 3 is a schematic cross-sectional view of a chip device in accordance with a first embodiment.

FIG. 3 shows a first embodiment of a chip device 20 (that may be used as a magnetic chip detector, as illustrated, or as a magnetic chip collector) where the step of subsequently magnetizing can be avoided and/or where the chip device 20 can have a greater resistance to demagnetization than the chip device of FIG. 2. Greater resistance to demagnetization can be particularly useful in aircraft engine applications where maintenance issues can be alleviated. Also, ambiguity in system performance or sensitivity to storing next to magnetic parts or minor moving magnetic fields such as transformers and motors can be removed. As detailed below, a described solution to at least some of the formerly identified issues lies in bridging the magnetic gap at the inner end of the rods to complete the magnetic circuit and in using a powerful rare earth magnet within the magnetic circuit.

The chip device 20 can be seen to have a magnetic circuit closing means, such as a horseshoe magnet 22, held within a housing 24. The horseshoe magnet 22 is made up of a plurality of portions (26, 28, 30, 32) which extend sequentially, end to end, in an arrangement forming a general U shape of the horseshoe magnet 22. The magnet 22 is 'powered' by one of the portions being a rare earth magnet portion 26 made of a rare earth magnet material having a dense magnetic flux. Rare earth magnet materials are often quite brittle and not very resistant to mechanical stress, henceforth, the rare earth magnet portion 26 is integrated within the housing 24 (which can be a potted housing) in this embodiment, and is thus mechanically protected by the housing 24. Two of the portions are end portions 28, 30 which protrude from the housing 24 and each lead to a corresponding one of the protruding tips 34, 36 (or magnetic poles) of the horseshoe magnet 22.

For the rare earth magnet portion 26 to properly 'power' the horseshoe magnet 22, a continuous magnetic path follows the length of the U shape between the two tips 34, 36. This can be achieved either by using portions made of a magnet alloy, which become charged by the rare earth magnet portion 26 automatically after assembly (rather than by requiring a subsequent magnetization step), or simply by using portions which are of a magnetically permeable material and which form magnetically permeable guides to the magnetic field generated by the rare earth magnet portion 26.

In the embodiment shown in FIG. 3, the horseshoe magnet 22 includes a first end portion 28, in a form of a rod made of a magnet alloy and forming a first arm of the U shape, a second end portion 30 in the form of a short rod made of a magnet alloy and forming, together with the rare earth portion 26, a second arm of the U shape (i.e. the rare earth portion 26 is also provided in the form of a short rod positioned immediately behind the second end portion 30 to collectively achieve a length comparable to the length of the first end portion 28), and a connector portion 32 magnetically connecting the two arms of the U shape. In this embodiment, the connector portion 32 is C-shaped. Each one of the portions 28, 32, 26, 30 can be integrated into a potted housing, for instance. Henceforth, after potting, even if the first end portion 28 and the second end portion 30 are not magnetized, they can become 'magnetically charged' slowly, but automatically, and potentially to a fixed value, by the magnetic power of the rare earth magnet. The magnetic power of the rare earth magnet indeed acts directly upon the second end portion 30, and also acts on the first end portion 28 via the connector portion 32 or other magnetically permeable guide. Moreover, when using magnet rods such as ALNICO V (Registered Trademark), the magnet rods can 'heal' by being re-magnetized in the event of demagnetization.

In order to achieve satisfactory results, a rare earth magnet having very high coercive force (Hc) (e.g. as typically obtained from SaCo or Neodymium magnet alloys) can be used. For instance, a typical ALNICO alloy can have an Hc of 640 whereas a typical Samarium Cobalt (SaCo) magnet alloy can have an Hc of 9200.

In an alternate embodiment, the first end portion 28 and the second end portion 30 can be made of a magnetically permeable material rather than a magnet alloy, and the magnetic power of the rare earth magnet, extending to the poles via the magnetically permeable guides, can provide a satisfactory amount of magnetic attraction. In other words, in this alternate embodiment, the high density rare earth magnet imposes a static magnetic flux which is guided by the magnetically permeable rods so as to create the desired flux pattern between the exposed rod tips 34, 36. An optional flux guide can be used within the chip device 20 and positioned so as to guide the flux path inside the device. Alternately, the flux guide at the rod ends can be replaced with a high density rare earth type magnet. If it is desired to achieve a specific flux strength, the flux strength can be adapted during assembly such as by leaving a specific amount of internal air gap(s) between the portions. By reducing the inside air gap, the flux strength at the external tips is increased, permitting a smaller internal magnet for a given flux strength. Alternately, the strength of the flux at the rod tips can be adjusted downward by increasing any of the gaps in the magnetic circuit such as between the magnet and the permeable rods. The strength of the flux at the rod tips 34, 36 can also be adjusted downward by shunting it away.

It should be understood that alternate configurations may apply. For example, the rare earth portion 26 may be made full length and the second end portion 30 eliminated. Also, a bore may be formed in the second end portion 30 (by rifle drilling or any other suitable process) and a thin cylinder magnet inserted into the bore. A non permeable sheath may further be used. Also, any means, other than the horseshoe magnet 22, suitable for closing the magnetic circuit within the chip device 20 may apply. Still, regardless of the configuration of the chip device 20, it is desirable to ensure electrical isolation between the poles with closed magnetic circuit adjacent an end (e.g. proximal) of the chip device 20.

In the specific embodiment shown in FIG. 3, the chip detection can be performed without removing the chip device 20 from the oil compartment or line of the gas turbine engine. To this end, the two tips 34, 36 are electrically insulated from one another, which can be achieved by using an electrical insulator 38 between two of the portions of the horseshoe magnet 22. In this manner, internal electrical shorting is avoided by the use of the insulating material. In this embodiment, an electrical insulator 38 such as a polyimide sheet is used between the connector portion 32 and both the first arm and the second arm and an appropriate housing 24 is used. Independent electrical connections 40, 42 can thus be established with corresponding ones of the tips 34, 36, and continuity can be checked to determine whether or not the presence of an electrically conductive chip bridges the gap between the two tips 34, 36, thereby closing the electrical circuit therebetween. In this embodiment, the electrical connections 40, 42 are achieved by way of corresponding electrical contact wires each connecting a corresponding arm of the U shape.

Figure 4:
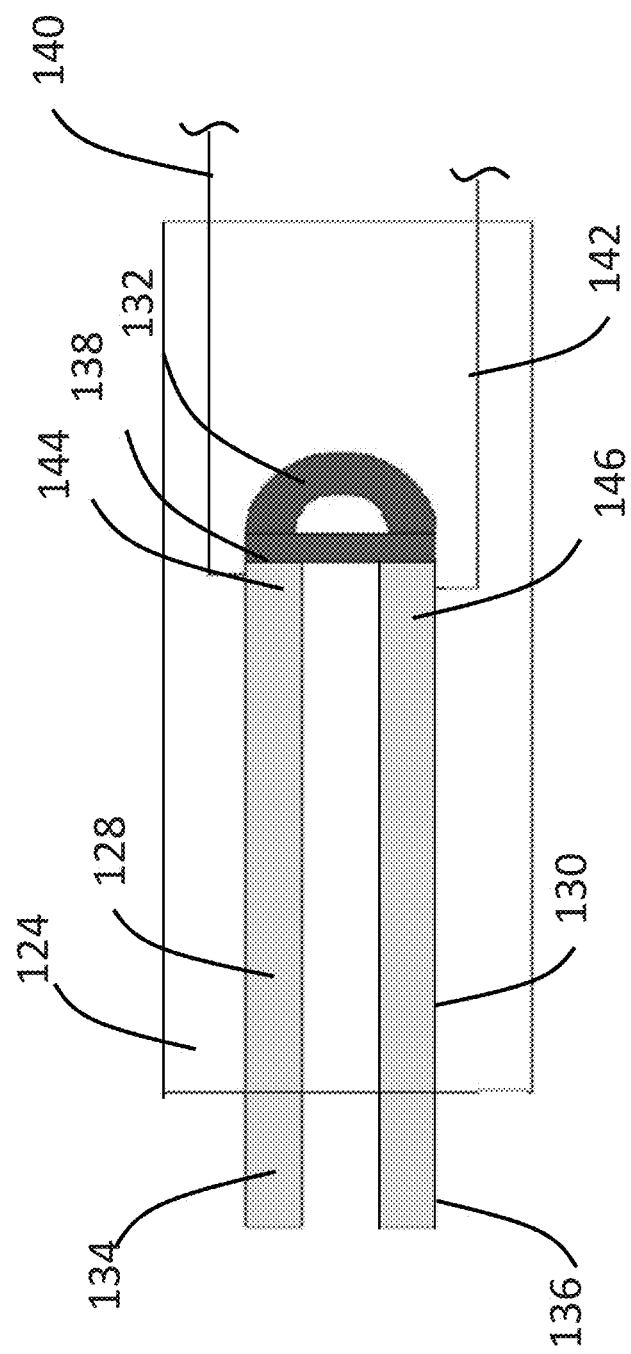
FIG. 4 is a schematic cross-sectional view of a chip device in accordance with a second embodiment.

Another embodiment is shown in FIG. 4. In this embodiment, two rods 128, 130 are used, each forming a corresponding end portion and a corresponding arm of the U-shape and each having a corresponding distal end 134, 136 protruding from the housing 124 for exposure to metal chips. The rods 128, 130 are made of a magnetically permeable material. A rare earth magnet portion 132 is used to bridge the proximal ends 144, 146 of the rods and charge the magnetic poles, the rods 128, 130 thus acting as magnetic guides, or magnetic shunts between the rare earth magnet portion 132 and the magnetic poles at the distal ends 134, 136. A magnetic insulator 138 and an appropriate housing 124 isolates the rods 128, 130 from one another, allowing independent connection by electrical wires 140, 142. In this specific embodiment, the rare earth magnet portion 132 is C-shaped, either mechanically or magnetically. Still, it will be understood that, in alternate embodiments, the rare earth magnet portion 132 can be short-bar shaped or have another suitable shape having distinct north and south polarity associated to corresponding ones of the proximal ends 144, 146.

This configuration using an embedded rare-earth magnet magnetically coupling the inner ends of rods can have a remarkably high resistance to demagnetization from external magnetic fields (static or moving), or from shock (as the rare-earth magnet is embedded and partly decoupled). Sensitivity to heat can be a negligible issue in the case where the device is used in an oil-cooled environment where environmental temperatures are below the level required to threaten the charge level. In this embodiment, the rare earth magnet is a SaCo magnet having a Curie temperature of 800° C. well adapted for practical working in maximum temperatures ranging between 300 and 550° C., the magnetically permeable material is permendur, and the electrical insulator is a polyimide film, more specifically Kapton, trademark of DuPont. It will be understood that other materials and shapes can be used in alternate embodiments. An embodiment using permendur rods can be substantially insensitive to brazing, which can be another improvement over previously known designs which were sensitive to braze process variations. Moreover, plating the protruding distal ends 134, 136 with a durable coating made of an electrically conductive and magnetically permeable metal (e.g. Nickel) that can provide a relatively high spark erosion resistance. During assembly, a spacer made of Torlon or another temperature-resistant, non-conductive, non-magnetically permeable material can be used to avoid the magnet clinging during assembly.

Figure 5:
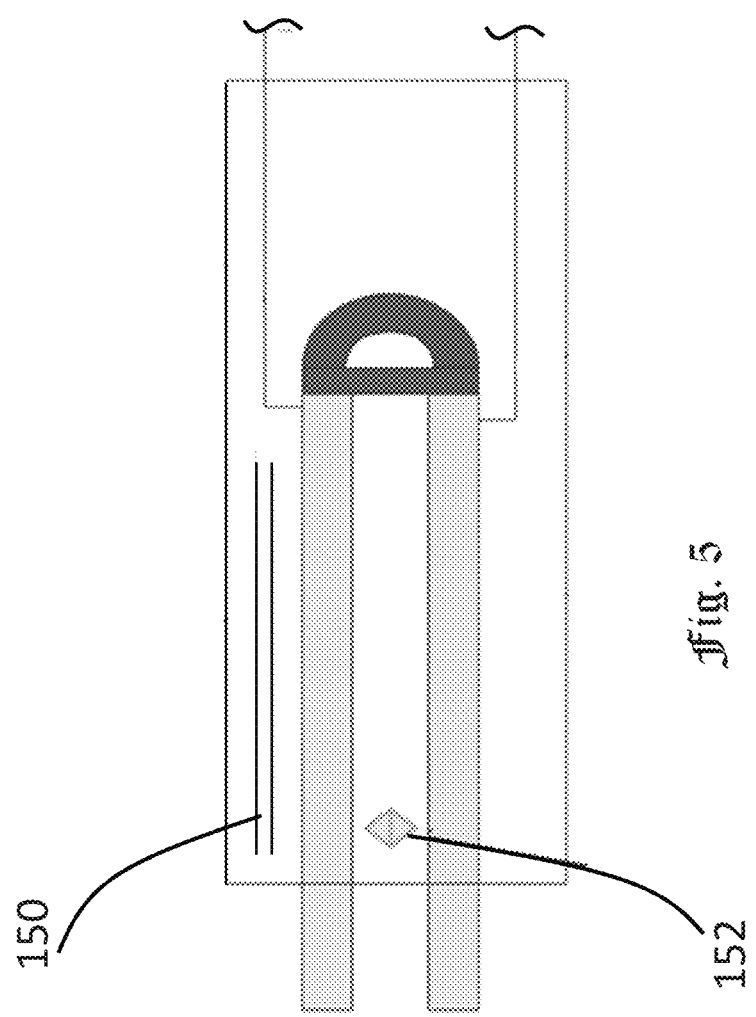
FIG. 5 is a schematic cross-sectional view of a chip device in accordance with a third embodiment.

The general configuration of the embodiment shown in FIG. 5 has similarities with the configuration of the embodiment shown in FIG. 4. However, the embodiment shown in FIG. 5 was designed with a magnetic shielding 150 to illustrate a possible embodiment. Moreover, one or more high density magnet(s), with or without passive flux guides, can be used with a shunt 152 of selected permeability positioned below the level of the protruding distal ends (e.g. embedded within the housing). Such a configuration can result in a 'race track' of remarkably high flux density but with a secondary path of selected flux density at the working tips placed in the oil passage. This configuration can achieve satisfactory resistance to demagnetization as it can achieve satisfactory low magnetic interaction with the outside world.

In other embodiments, the chip device's hollow housing (reference 24 in FIG. 3 and 124 in FIG. 4) may be made of or coated with an electrically conductive and magnetically permeable material so as to form one magnetic pole. A rod may then be positioned within the housing concentrically therewith so as to form the other magnetic pole. In this configuration (not shown), any magnetic metal chip that shorts the center rod to any periphery of the housing completes a magnetic circuit and also an electrical circuit. Indeed, the housing would in this embodiment behave as the first electrical connection (e.g. ground) while the centered rod would behave as the second electrical connection.

If designing a drop-in device intended to replace a prior art plug-type detector device, for instance, adequately identical dimensions and magnetic properties can be achieved in order to avoid any engine level re-substantiation or airframe interface issues either direct or by a change of performance.

The above description is meant to be exemplary only, and one skilled in the art will recognize that changes may be made to the embodiments described without departing from the scope of the invention disclosed. For example, although embodiments described above in FIGS. 3 to 5 have wires for automated electrical detection of chips, alternate embodiments can be wire-free and adapted solely for visual inspection or chip collection, for instance. Still other modifications which fall within the scope of the present invention will be apparent to those skilled in the art, in light of a review of this disclosure, and such modifications are intended to fall within the scope of the appended claims.

What is claimed is:

1. A gas turbine engine comprising:
   an oil system; and
   a magnetic chip device configured to provide an indication as to a presence of one or more metal chips in oil of the oil system, the magnetic chip device comprising a magnet held within a housing and having two adjacent tips adjacent a first end of the housing, the tips exposed to the oil for magnetically attracting the one or more metal chips, the magnet being generally U-shaped and having a plurality of portions extending sequentially from one of the tips to the other, following the U-shape, the plurality of portions including two end portions adjacent a second end of the housing opposite to the first end, the two end portions having a magnetic gap therebetween, each one of the two end portions extending to a corresponding one of the tips, and a rare-earth magnet portion made of a rare earth magnet material and positioned between the two end portions in the sequence, the rare earth magnet portion configured to bridge the magnetic gap and create a continuous magnetic path along a length of the U-shape, thereby automatically magnetizing the magnet.

2. The gas turbine engine of claim 1 wherein the rare-earth magnet portion is positioned between a first arm of the U-shape and a second arm of the U-shape and has opposite poles each associated to a corresponding one of the arms.

3. The gas turbine engine of claim 2 wherein the rare-earth magnet portion is C-shaped and magnetically connects both arms of the U-shape.

4. The gas turbine engine of claim 1 further wherein the plurality of portions further comprises a connector portion made of a magnetically permeable guide, the connector portion being intermediate to and magnetically completing a magnetic circuit between a first arm of the U-shape and a second arm of the U-shape.

5. The gas turbine engine of claim 4 wherein the connector portion is C-shaped.

6. The gas turbine engine of claim 1 wherein the end portions are made of a magnetically permeable material.

7. The gas turbine engine of claim 6 wherein the tips are coated with a spark erosion resistant, electrically conductive, and magnetically permeable metal.

8. The gas turbine engine of claim 1 wherein the end portions are made of a magnet alloy and are magnetically charged by the rare earth magnet material.

9. The gas turbine engine of claim 1 further comprising an electrical insulator positioned between the two end portions in the sequence and electrically insulating the end portions from one another, and at least one pair of electrical connections, each one of the electrical connections of the at least one pair being electrically connected to a corresponding one of the end portions.

10. A magnetic chip device comprising: a magnet configured to provide an indication as to a presence of one or more metal chips in oil, the magnet held within a housing and having two adjacent tips protruding away from a first end of the housing into the oil for magnetically attracting the one or more metal chips, the magnet being generally U-shaped and having a plurality of portions extending sequentially from one of the tips to the other, following the U-shape, the plurality of portions including two end portions adjacent a second end of the housing opposite to the first end, the two end portions having a magnetic gap therebetween, each one of the two end portions extending to a corresponding one of the tips, and a rare earth magnet portion made of a rare earth magnet material and positioned between the two end portions in the sequence, the rare earth magnet portion configured to bridge the magnetic gap and create a continuous magnetic path along a length of the U-shape, thereby automatically magnetizing the magnet.

11. The magnetic chip device of claim 10 wherein the rare-earth magnet portion is positioned between a first arm of the U-shape and a second arm of the U-shape and has opposite poles each associated to a corresponding one of the arms.

12. The magnetic chip device of claim 11 wherein the rare-earth magnet portion is C-shaped and magnetically connects both arms of the U-shape.

13. The magnetic chip device of claim 10 further wherein the plurality of portions further comprises a connector portion made of a magnetically permeable guide, the connector portion being intermediate to and magnetically completing a magnetic circuit between a first arm of the U-shape and a second arm of the U-shape.

14. The magnetic chip device of claim 13 wherein the connector portion is C-shaped.

15. The magnetic chip device of claim 10 wherein the end portions are made of a magnetically permeable material.

16. The magnetic chip device of claim 15 wherein the tips are coated with a spark erosion resistant, electrically conductive, and magnetically permeable metal.

17. The magnetic chip device of claim 10 wherein the end portions are made of a magnet alloy and are magnetically charged by the rare earth magnet material.

18. The magnetic chip device of claim 10 further comprising an electrical insulator positioned between the two end portions in the sequence and electrically insulating the end portions from one another, and at least one pair of electrical connections, each one of the electrical connections of the at least one pair being electrically connected to a corresponding one of the end portions.

19. The magnetic chip device of claim 10 further comprising a shunt of predetermined permeability positioned between the two end portions, within the housing.

20. The magnetic chip device of claim 10 wherein the housing is a potted housing.

* * * * *